US006635772B2

(12) United States Patent
Hayashibara et al.

(10) Patent No.: US 6,635,772 B2
(45) Date of Patent: Oct. 21, 2003

(54) METHOD FOR PRODUCING CHROMAN-CARBOXYLIC ACID

(75) Inventors: Tatsuhiko Hayashibara, Kitakanbara-gun (JP); Junko Sato, Kitakanbara-gun (JP); Masahiro Torihara, Kitakanbara-gun (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 09/939,803

(22) Filed: Aug. 28, 2001

(65) Prior Publication Data
US 2002/0035276 A1 Mar. 21, 2002

(30) Foreign Application Priority Data
Aug. 29, 2000 (JP) ........................................ 2000-259565

(51) Int. Cl.$^7$ ........................ C07D 311/76; C07C 43/00
(52) U.S. Cl. ........................ 549/405; 568/602
(58) Field of Search ....................... 549/405; 568/662

(56) References Cited

U.S. PATENT DOCUMENTS

| 3,291,841 A | * 12/1966 | O'Shea | 568/662 |
| 3,291,842 A | * 12/1966 | O'Shea | 569/662 |
| 3,947,473 A | * 3/1976 | Scott et al. | 549/405 |
| 4,003,919 A | * 1/1977 | Scott et al. | 549/405 |
| 4,745,114 A | 5/1988 | Elliott et al. | |
| 5,646,308 A | * 7/1997 | Koga et al. | 549/405 |
| 6,136,986 A | * 10/2000 | Stumer et al. | 549/405 |

FOREIGN PATENT DOCUMENTS

| EP | 0 115 142 | 8/1984 |
| EP | 0 645 383 | 3/1995 |
| EP | 0 891 974 | 1/1999 |
| WO | WO 99/32475 | 7/1999 |

OTHER PUBLICATIONS

Kostas Karabelas, et al., J. Am. Chem. Soc. vol. 112, pp. 5372–5373, "((Trimethylsilyl)Methyl)–1,4–Benzoquinones. Generation and Trapping of 0–Quinone Methides", 1990.

Donald T. Witlak, et al., Journal of Medicinal Chemistry, vol. 14, No. 8, pp. 758–766, "6–Chlorochroman–2–Carboxylic Acids. Synthesis and Biological Evaluation as Antagonists for Cholesterol Biosynthesis and Lipolysis in Vitro", 1971.

* cited by examiner

Primary Examiner—Alan L. Rotman
Assistant Examiner—Raymond Covington
(74) Attorney, Agent, or Firm—Oblon, Spivak, McClelland, Maier & Neustadt, P.C.

(57) ABSTRACT

A method for producing a chroman-carboxylic acid is provided, which method includes reacting a dialkylphenol compound, a formaldehyde and an alcohol in the presence of a secondary amine and an acid to give an alkoxymethylated phenol compound (Step 1); reacting the obtained alkoxymethylated phenol compound with an ester having a carbon-carbon double bond at a temperature of not less than 100° C. to give a dialkylchroman carboxylic acid ester (Step 2); hydrolyzing the obtained dialkylchroman carboxylic acid ester to give a dialkylchroman-carboxylic acid (Step 3); and reacting the obtained dialkylchroman-carboxylic acid with an aromatic hydrocarbon in the presence of a Lewis acid (Step 4).

19 Claims, No Drawings

METHOD FOR PRODUCING CHROMAN-CARBOXYLIC ACID

TECHNICAL FIELD OF THE INVENTION

The present invention relates to a method for producing chroman-carboxylic acid and a novel intermediate useful for the synthesis of chroman-carboxylic acid. The chroman-carboxylic acid is useful as, for example, a starting material of pharmaceutical products (WO99/32475) showing $\beta_3$-adrenoreceptor activity, a starting material of pharmaceutical products (EP 0 115 142) having $\alpha_2$-antagonism, and a starting material for the synthesis of a fungicide (U.S. Pat. No. 4,745,114).

BACKGROUND OF THE INVENTION

As a production method of chroman-carboxylic acid, there are conventionally known (1) a method comprising obtaining 4-oxochromene-carboxylic acid from diethyl oxalate and 2-hydroxyacetophenone, and hydrogenating this 4-oxochromene-carboxylic acid (JP-A-59-130286), and (2) a method comprising obtaining phenoxylactone from bromobutyrolactone and phenol, and reducing the phenoxylactone (J. Med. Chem., vol. 14, pp. 758–766 (1971)). In addition, EP 0 891 974 discloses a production method of a chroman compound, which comprises reacting a phenol compound wherein at least one ortho position relative to a phenolic hydroxyl group is not substituted, a formaldehyde and an alcohol to give an alkoxymethylated phenol compound, and reacting the obtained alkoxymethylated phenol compound with a compound having a carbon-carbon double bond but without, in a molecule, a hydroxyl group or an electron withdrawing group directly bonded to a carbon atom constituting the carbon-carbon double bond.

However, the above-mentioned method (1) uses a large amount of acid and base, as well as poisonous oxalic acid ester, and the method (2) uses expensive bromobutyrolactone. Neither of them is an industrially advantageous method.

SUMMARY OF THE INVENTION

It is therefore an object of the present invention to provide a method for producing chroman-carboxylic acid smoothly and easily in a high yield with high industrial productivity from an easily obtainable starting material or an economical starting material.

According to the present invention, there has now been found that, by reacting an easily obtainable and economical dialkylphenol compound, a formaldehyde and an alcohol in the presence of a secondary amine and an acid, an alkoxymethylated phenol compound, wherein the ortho position relative to the phenolic hydroxyl group is alkoxymethylated, can be obtained (Step 1); by reacting the obtained alkoxymethylated phenol compound with an ester having a carbon-carbon double bond at a temperature of not less than 100° C., a dialkylchroman carboxylic acid ester can be obtained (Step 2); by hydrolyzing the obtained dialkylchroman carboxylic acid ester, a dialkylchroman-carboxylic acid can be obtained (Step 3); and by reacting the obtained dialkylchroman-carboxylic acid with an aromatic hydrocarbon in the presence of a Lewis acid, chroman-carboxylic acid can be obtained smoothly in a high yield (Step 4).

It has been also found that, by reacting, in Step 2, an alkoxymethylated phenol compound and an ester having a carbon-carbon double bond in the presence of an acid, the reaction can be accelerated.

It has been further found that a specific synthetic intermediate in the production method of chroman-carboxylic acid, which comprises the above-mentioned 4 reaction steps, is a novel compound.

That is, the present invention provides a method for producing a chroman-carboxylic acid of the formula (II)

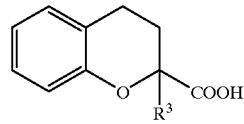

(II)

wherein $R^3$ is a hydrogen atom or an alkyl group [hereinafter to be referred to as chroman-carboxylic acid (II)], which method comprises reacting a dialkylchroman-carboxylic acid of the formula (I)

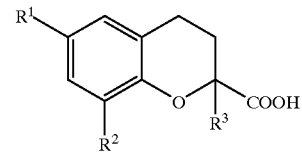

(I)

wherein $R^1$ and $R^2$ are each independently an alkyl group and $R^3$ is as defined above [hereinafter to be referred to as dialkylchroman-carboxylic acid (I)] with an aromatic hydrocarbon in the presence of a Lewis acid.

The present invention also provides a method for producing a chroman-carboxylic acid (II), which method comprises reacting a dialkylphenol compound of the formula

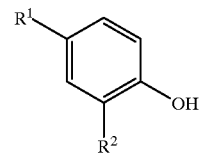

(III)

wherein $R^1$ and $R^2$ are as defined above [hereinafter to be referred to as dialkylphenol compound (III)], a formaldehyde and an alcohol in the presence of a secondary amine and an acid to give an alkoxymethylated phenol compound of the formula (IV)

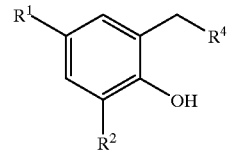

(IV)

wherein $R^1$ and $R^2$ are as defined above and $R^4$ is an alkoxyl group [hereinafter to be referred to as alkoxymethylated phenol compound (IV)]; reacting the obtained alkoxymethylated phenol compound (IV) with an ester of the formula (V)

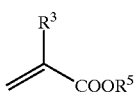

(V)

wherein $R^3$ is as defined above and $R^5$ is an alkyl group or an aralkyl group, having a carbon-carbon double bond [hereinafter to be referred to as unsaturated ester (V)] at a temperature of not less than 100° C. to give a dialkylchroman carboxylic acid ester of the formula (VI)

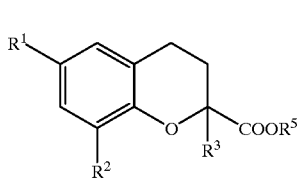

(VI)

wherein $R^1$, $R^2$, $R^3$ and $R^5$ are as defined above [hereinafter to be referred to as dialkylchroman carboxylic acid ester (VI)]; hydrolyzing the obtained dialkylchroman carboxylic acid ester (VI) to give a dialkylchroman-carboxylic acid (I); and reacting the obtained dialkylchroman-carboxylic acid (I) with an aromatic hydrocarbon in the presence of a Lewis acid.

The present invention also provides dialkylchroman-carboxylic acid (I) and an alkoxymethylated phenol compound (IV).

The present invention further provides a method for producing dialkylchroman-carboxylic acid (I), which method comprising reacting dialkylphenol compound (III), a formaldehyde and an alcohol in the presence of a secondary amine and an acid to give alkoxymethylated phenol compound (IV); reacting the obtained alkoxymethylated phenol compound (IV) with unsaturated ester (V) at a temperature of not less than 100° C. to give dialkylchroman carboxylic acid ester (VI); and hydrolyzing the obtained dialkylchroman carboxylic acid ester (VI).

DETAILED DESCRIPTION OF THE INVENTION

In the above-mentioned formulas, the alkyl group represented by $R^1$, $R^2$, $R^3$ and $R^5$ is preferably straight or branched chain alkyl group having 1 to 8 carbon atoms, such as methyl group, ethyl group, propyl group, isopropyl group, butyl group, isobutyl group, t-butyl group, hexyl group, 2-ethylhexyl group, octyl group and the like. The alkoxyl group represented by $R^4$ is preferably alkoxyl group having 1 to 8 carbon atoms, such as methoxy group, ethoxy group, 1-propoxy group, 1-butoxy group, 1-hexanoxy group, 1-octanoxy group, 2-ethyl-1-hexanoxy group, 2-propoxy group, 2-butoxy group, cyclohexanoxy group, 2-hydroxy-1-ethoxy group, 4-hydroxy-1-butoxy group, 6-hydroxy-1-hexanoxy group, benzyloxy group, phenethyloxy group and the like. The aralkyl group represented by $R^5$ is preferably aralkyl group wherein the aryl moiety has 6 to 14 carbon atoms and the alkyl moiety has 1 to 6 carbon atoms, such as benzyl group, phenethyl group and the like.

In the above-mentioned Step 1, dialkylphenol compound (III), a formaldehyde and an alcohol are reacted in the presence of a secondary amine and an acid to give alkoxymethylated phenol compound (IV). This alkoxymethylated phenol compound (IV) is novel and is provided for the first time by the present invention.

Examples of formaldehyde include linear polymers of formalin such as formalin, paraformaldehyde and the like; cyclic acetal oligomers such as trioxane, tetraoxane and the like; and the like. These formaldehydes may be used solely or in combination of two or more thereof.

Examples of alcohol include saturated aliphatic primary alcohols such as methanol, ethanol, 1-propanol, 1-butanol, 1-hexanol, 1-octanol, 2-ethyl-1-hexanol and the like; saturated aliphatic secondary alcohols such as 2-propanol, 2-butanol, cyclohexanol and the like; saturated aliphatic diols such as ethylene glycol, 1,4-butanediol, hexylenediol and the like; aralkyl alcohols such as benzyl alcohol, phenethyl alcohol and the like; and the like. These alcohols may be used solely or in combination of two or more thereof. The alkoxyl group at $R^4$ in the above-mentioned formula (IV) is derived from the aforementioned alcohol.

The above-mentioned secondary amine and acid act as a catalyst and/or a promoter to generate an alkoxymethylated phenol compound.

As the secondary amine, any of aliphatic secondary amine and aromatic secondary amine can be used without limitation on the kind thereof. Examples of the secondary amine include chain aliphatic secondary amines such as diethylamine, dibutylamine, bis(2-ethylhexyl)amine, dioctylamine and the like; cyclic aliphatic secondary amines such as piperidine, pyrrolidine, morpholine and the like; aromatic secondary amines such as N-methylaniline, N-ethylaniline and the like; and the like. These secondary amines may be used solely or in combination of two or more thereof.

As the acid, any of organic acid and inorganic acid can be used. Organic acid is preferably used from the aspect of selectivity. Particularly, saturated fatty acid having 2 to 8 carbon atoms and aromatic fatty acid are preferably used. Examples of the organic acid include acetic acid, propionic acid, butyric acid, 2-methylpropanoic acid, valeric acid, 3-methylbutanoic acid, 2-methylbutanoic acid, hexanoic acid, heptanoic acid, octanoic acid, benzoic acid and the like. These acids may be used solely or in combination of two or more thereof.

For smooth production of alkoxymethylated phenol compound (IV) in the reaction of Step 1, the formaldehyde is preferably used in an amount of 0.8–10 equivalents, more preferably 1–2 equivalents, the alcohol is preferably used in an amount of 0.8–20 equivalents, more preferably 1–10 equivalents, the secondary amine is preferably used in an amount of 0.001–1 equivalent, more preferably 0.01–0.5 equivalent, and the acid is preferably used in an amount of 0.01–5 equivalents, more preferably 0.1–1.0 equivalent, all of which per 1 equivalent of dialkylphenol compound (III).

The reaction of Step 1 can be carried out in the presence or absence of a solvent. Examples of the solvent include inert solvents such as toluene, xylene, N-methylpyrrolidone and the like. The solvent is preferably used in an amount of 50–1000 parts by weight per 100 parts by weight of dialkylphenol compound (III).

The reaction of Step 1 is carried out by mixing dialkylphenol compound (III), a formaldehyde, an alcohol, a secondary amine, an acid and, where necessary, a solvent. The reaction temperature is preferably 50–150° C., more preferably 80–120° C. When the boiling point of the alcohol to be used is lower than the aforementioned reaction temperature, the reaction is preferably carried out under pressure. While the reaction time varies depending on the kind of dialkylphenol compound (III), formaldehyde, alcohol, secondary amine and acid to be used, it is preferably 30 min–24 h.

In the reaction of Step 1, water is produced as a byproduct. Removal of water from the reaction system during the reaction shortens the reaction time.

In Step 2, alkoxymethylated phenol compound (IV) obtained in Step 1 is reacted with unsaturated ester (V) at a temperature of not less than 100° C. to give dialkylchroman carboxylic acid ester (VI).

The alkoxymethylated phenol compound (IV) obtained in Step 1 may be used in Step 2 without isolation from the reaction mixture. For smooth production of dialkylchroman carboxylic acid ester (VI) in a high yield, however, the produced alkoxymethylated phenol compound (IV) is isolated from the reaction mixture of Step 1, and where necessary, purified before use. The method for isolating alkoxymethylated phenol compound (IV) from the reaction mixture of Step 1 may include extraction with a solvent such as aromatic hydrocarbon (e.g., toluene, xylene and the like); ether (e.g., diisopropyl ether and the like); and the like, vacuum distillation, and the like.

In Step 2, at least one kind of unsaturated ester (V) can be used. The unsaturated ester (V) for smooth production of dialkylchroman carboxylic acid ester (VI) is preferably used in an amount of 0.8–20 equivalents, more preferably 1.0–10 equivalents, relative to alkoxymethylated phenol compound (IV).

The reaction of Step 2 is preferably carried out in the absence of a solvent, but may be carried out in the presence of a solvent. When the reaction is carried out in the presence of a solvent, for example, an inert solvent such as decalin, mesitylene, N-methylpyrrolidone and the like is preferably used. A solvent is preferably used in an amount of 50–500 parts by weight per 100 parts by weight of alkoxymethylated phenol compound (IV).

The reaction of Step 2 is preferably carried out in the presence of an acid. The acid acts as a catalyst and/or a promoter for producing dialkylchroman carboxylic acid ester (VI). As the acid, any of organic acid and inorganic acid can be used, but from the aspect of selectivity, an organic acid is preferably used. In particular, saturated fatty acid having 2 to 8 carbon atoms and aromatic fatty acid are preferably used. Examples of such acid include acetic acid, propionic acid, butyric acid, 2-methylpropanoic acid, valeric acid, 3-methylbutanoic acid, 2-methylbutanoic acid, hexanoic acid, heptanoic acid, octanoic acid, benzoic acid and the like. These acids may be used solely or in combination of two or more thereof. The acid is preferably used in an amount of 0.1–100 mol %, more preferably 1–10 mol %, relative to alkoxymethylated phenol compound (IV).

The reaction of Step 2 is carried out by mixing alkoxymethylated phenol compound (IV), unsaturated ester (V), and where necessary, an acid and a solvent at a temperature of 100° C. or higher. The reaction temperature is preferably 100–250° C., more preferably 120–200° C. When the boiling point of the unsaturated ester (V) to be used is lower than the aforementioned reaction temperature, the reaction is preferably carried out under pressure. While the reaction time varies depending on the kind of alkoxymethylated phenol compound (IV) and unsaturated ester (V) to be used, it is preferably 30 min–48 h.

In the reaction of Step 2, alcohol is produced as a byproduct. Removal of alcohol from the reaction system during the reaction shortens the reaction time.

In Step 3, dialkylchroman carboxylic acid ester (VI) obtained in Step 2 is hydrolyzed to give dialkylchroman-carboxylic acid (I). This dialkylchroman-carboxylic acid (I) is novel and is provided for the first time by the present invention.

The dialkylchroman carboxylic acid ester (VI) obtained in Step 2 may be used in Step 3 without isolation from the reaction mixture. However, the produced dialkylchroman carboxylic acid ester (VI) is preferably isolated from the reaction mixture of Step 2, and where necessary, purified before use. The method for isolating dialkylchroman carboxylic acid ester from the reaction mixture of Step 2 may include extraction with a solvent such as aromatic hydrocarbon (e.g., toluene, xylene and the like); ether (e.g., diisopropyl ether and the like); and the like, vacuum distillation, and the like.

The hydrolysis reaction in Step 3 is preferably carried out in the presence of an acid or a base, particularly in the presence of a base.

While the kind of acid is not particularly limited, for example, mineral acid such as hydrochloric acid, sulfuric acid and the like; organic acid such as paratoluenesulfonic acid and the like; and the like are used. The acid is preferably used in an amount of 0.1 to 10 mol, per 1 mol of dialkylchroman carboxylic acid ester (VI).

While the kind of base is not particularly limited, for example, alkaline metal hydroxide such as sodium hydroxide, potassium hydroxide, lithium hydroxide and the like; alkaline earth metal hydroxide such as calcium hydroxide, magnesium hydroxide, barium hydroxide and the like; and the like are used. The base is preferably used in an amount of 0.7–5 mol, more preferably 1.0–3 mol, per 1 mol of dialkylchroman carboxylic acid ester (VI).

In Step 3, alcohol can be added to the reaction system for smooth progress of the hydrolysis reaction. While the kind of alcohol is not particularly limited, for example, saturated aliphatic primary alcohol such as methanol, ethanol, 1-propanol, 1-butanol, 1-hexanol, 1-octanol, 2-ethyl-1-hexanol and the like; saturated aliphatic secondary alcohol such as 2-propanol, 2-butanol, cyclohexanol and the like; saturated aliphatic diol such as ethylene glycol, 1,4-butanediol, hexylenediol and the like; and the like are used. The alcohol is preferably used in an amount of 0.5 to 10 parts by weight, more preferably 1.0 to 3 parts by weight, per one part by weight of dialkylchroman carboxylic acid ester (VI).

The reaction of Step 3 is carried out by mixing dialkylchroman carboxylic acid ester (VI), water and, where necessary, an acid or a base and an alcohol. The reaction temperature is preferably 20–120° C., more preferably 50–100° C. When the reaction proceeds at a temperature higher than the boiling point of the alcohol and water to be used, the reaction is preferably carried out under pressure. While the reaction time varies depending on the kind of dialkylchroman carboxylic acid ester (VI), it is preferably 30 min–48 h.

In Step 4, dialkylchroman-carboxylic acid (I) obtained in Step 3 is reacted with an aromatic hydrocarbon in the presence of a Lewis acid to give chroman-carboxylic acid (II).

The dialkylchroman-carboxylic acid (I) obtained in the above-mentioned Step 3 may be used in Step 4 without isolation from the reaction mixture. However, it is preferably isolated from the reaction mixture, and where necessary, purified before use. The method for isolation may include extraction with a solvent such as aromatic hydrocarbon (e.g., toluene, xylene and the like); ether (e.g., diisopropyl ether and the like); and the like, vacuum distillation, and the like.

When the hydrolysis is performed in the presence of a base, the produced dialkylchroman carboxylic acid salt is preferably dissolved in an aqueous layer and extracted with an organic solvent to remove impurities such as polymer and the like.

In Step 4, the Lewis acid acts as a catalyst and/or a promoter to produce chroman-carboxylic acid. As the Lewis acid, metal chloride is preferably used. While the kind thereof is not particularly limited, aluminum chloride, zinc chloride, iron chloride and the like are exemplified. These Lewis acids may be used solely or in combination of two or more thereof.

The Lewis acid, for smooth production of chroman-carboxylic acid (II), is preferably used in an amount of 0.1–5 equivalents, more preferably 0.5–2 equivalents, per 1 equivalent of dialkylchroman-carboxylic acid (I).

While the kind of aromatic hydrocarbon is not particularly limited, for smooth production of chroman-carboxylic acid (II), for example, aromatic hydrocarbon having electron-donating substituents, such as toluene, xylene, cumene and the like, is preferably used. These aromatic hydrocarbons may be used solely or in combination of two or more thereof.

The aromatic hydrocarbon, for smooth production of chroman-carboxylic acid (II), is preferably used in the largest possible amount. In view of the economical aspect, however, it is preferably 1–100 equivalents, more preferably 2–50 equivalents, per 1 equivalent of dialkylchroman-carboxylic acid (I).

The reaction of Step 4 is preferably carried out in the absence of a solvent, but may be carried out in the presence of a solvent. When the reaction is carried out in the presence of a solvent, for example, an inert solvent, such as hexane, heptane and the like, is preferably used. A solvent is preferably used in an amount of 50–1000 parts by weight per 100 parts by weight of dialkylchroman-carboxylic acid (I).

The reaction of Step 4 is carried out by mixing dialkylchroman-carboxylic acid (I), a Lewis acid, an aromatic hydrocarbon and, where necessary, a solvent. The reaction temperature is preferably 0–200° C., more preferably 10–140° C. When the boiling point of the aromatic hydrocarbon to be used is lower than the aforementioned reaction temperature, the reaction is preferably carried out under pressure. While the reaction time varies depending on the kind of dialkylchroman-carboxylic acid (I), it is preferably about 30 min-48 h.

The chroman-carboxylic acid (II) produced by the above-mentioned reaction may be isolated as necessary, and where the case demands, washed or crystallized for purification. The method for isolating chroman-carboxylic acid from the reaction mixture may include extraction with a solvent such as aromatic hydrocarbon (e.g., toluene, xylene and the like); ether (e.g., diisopropyl ether and the like); and the like, water and where necessary, by adding an acid or a base to the reaction mixture, vacuum distillation, and the like.

EXAMPLES

The present invention is explained in detail by referring to examples. The present invention is not limited by these examples in any way.

Example 1

Synthesis of 2,4-di-t-butyl-6-butoxymethyl-1-hydroxybenzene 2,4-di-t-Butylphenol (472.2 g, 2.29 mol), 87.3% paraformaldehyde (95.1 g, 2.77 mol), di-n-butylamine (29.6 g, 0.229 mol), acetic acid (69.8 g, 1.16 mol), 1-butanol (1183.1 g, 15.96 mol) and toluene were mixed and the mixture was refluxed under heating for 10 h. Water produced by the reaction was removed. After the completion of the reaction, the reaction mixture was washed successively with dilute aqueous sulfuric acid solution, aqueous sodium hydrogen carbonate solution and water, and the organic layer was concentrated under reduced pressure. The residue was quantitatively analyzed by liquid chromatography according to the internal standard method. As a result, 2,4-di-t-butyl-6-butoxymethyl-1-hydroxybenzene was obtained in a yield of 91%. The $^1$H-NMR data of the obtained 2,4-di-t-butyl-6-butoxymethyl-1-hydroxybenzene are shown in the following.

δ ppm (CDCl$_3$, 300 MHz) 7.27 (1H, d), 6.88 (1H, d), 4.68 (2H, s), 3.57 (2H, t, J=6.45 Hz), 1.5–1.8 (4H, m), 0.95 (3H, t, J=7.32 Hz), 1.44 (9H, s), 1.30 (9H, s)

Example 2

Synthesis of 6,8-di-t-butyl-2-butoxycarbonylchroman

Butyl acrylate (771.2 g, 6.02 mol) and benzoic acid (12.26 g, 0.10 mol) were added to 2,4-di-t-butyl-6-butoxymethyl-1-hydroxybenzene (665.2 g, net 586.71 g, 2.01 mol) obtained in Example 1, and the mixture was stirred while heating at 150–165° C. for 30 h. 1-Butanol produced by the reaction was removed. After the completion of the reaction, the reaction mixture was quantitatively analyzed by liquid chromatography according to the internal standard method. As a result, 6,8-di-t-butyl-2-butoxycarbonylchroman was obtained in a yield of 87% (1.74 mol). At this time, 6,8-di-t-butyl-3-butoxycarbonylchroman (a position isomer) was produced in about 8%. For use in the next step, excess butyl acrylate was distilled away under reduced pressure, toluene was added to the residue, and benzoic acid was removed with aqueous sodium hydrogen carbonate solution. The $^1$H-NMR data of the obtained 6,8-di-t-butyl-2-butoxycarbonylchroman are shown below.

δ ppm (CDCl$_3$, 300 MHz) 7.18 (1H, d), 6.90 (1H, d), 4.68 (1H, dd, J=3.48 Hz, J=5.01 Hz), 4.18–4.22 (2H, m), 2.79–2.90 (2H, m), 2.28 (1H, m), 2.18 (1H, m), 1.60–1.70 (4H, m), 1.43 (9H, s), 1.30 (9H, s), 0.92 (3H, t, J=7.41 Hz)

Example 3

Synthesis of 6,8-di-t-butyl-2-hydroxycarbonylchroman

To a toluene solution (183.0 g, 0.2 mol) of 6,8-di-t-butyl-2-butoxycarbonylchroman obtained in Example 2 were added 10% aqueous sodium hydroxide solution (120.0 g, 0.3 mol) and methanol (120 g), and the mixture was stirred while heating at 70° C. for 2 h. Toluene was added to the reaction mixture and the mixture was stirred and allowed to stand, and methanol and the like were removed from the aqueous layer. After the removal, aqueous sulfuric acid solution was added to the aqueous layer, and the mixture was extracted with toluene. The extract was concentrated under reduced pressure. The residue was quantitatively analyzed by liquid chromatography according to the internal standard method. As a result, 6,8-di-t-butyl-2-hydroxycarbonylchroman was obtained in a yield of 98% [net 56.92 g, 0.196 mol]. The $^1$H-NMR data of the obtained 6,8-di-t-butyl-2-hydroxycarbonylchroman are shown below.

δ ppm (CDCl$_3$, 300 MHz) 7.20 (1H, d), 6.93 (1H, d), 4.73 (1H, dd, J=3.45 Hz, J=5.19 Hz), 2.78–2.98 (2H, m), 2.29–2.41 (1H, m), 2.12–2.28 (1H, m), 1.42 (9H, s), 1.29 (9H, m)

Example 4

Synthesis of 2-chroman-carboxylic acid 6,8-di-t-Butyl-2-hydroxycarbonylchroman (2.90 g, 0.01 mol) obtained in Example 3 was dissolved in toluene (27 g), and the resulting solution was added dropwise to a suspension of aluminum chloride (2.67 g, 0.02 mol) in toluene at room temperature. After the dropwise addition, the mixture was stirred at room temperature for 2 h. The reaction mixture was poured into aqueous sulfuric acid solution and the organic layer was separated. An aqueous alkaline solution was added to the organic layer and the aqueous layer was separated. An aqueous sulfuric acid solution was added to the aqueous layer and the mixture was extracted with toluene. The extract was concentrated under reduced pressure. The residue was quantitatively analyzed by liquid chromatography according to the internal standard method.

As a result, 2-chroman-carboxylic acid was obtained in a yield of 90% [net 1.60 g, 0.009 mol]. The $^1$H-NMR data of the obtained 2-chroman-carboxylic acid are shown below.

δ ppm (CDCl$_3$, 300 MHz) 7.12 (2H, m), 6.92 (2H, m), 4.77 (1H, dd, J=3.57 Hz, J=4.38 Hz), 2.78–2.96 (2H, m), 2.32–2.42 (1H, m), 2.17–2.27 (1H, m)

According to the present invention, chroman-carboxylic acid can be obtained smoothly in a high yield with high productivity from easily obtainable starting materials and economical starting materials.

This application is based on a patent application No. 2000-259565 filed in Japan, the contents of which are hereby incorporated by reference.

What is claimed is:

1. A method for producing a chroman-carboxylic acid of the formula (II)

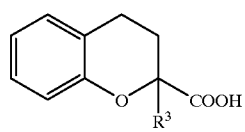

(II)

wherein R$^3$ is a hydrogen atom or an alkyl group, which method comprises reacting a dialkylchroman-carboxylic acid of the formula (I)

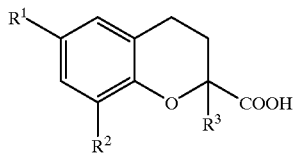

(I)

wherein R$^1$ and R$^2$ are each independently an alkyl group and R$^3$ is as defined above, with an aromatic hydrocarbon in the presence of a Lewis acid.

2. A method for producing a chroman-carboxylic acid of the formula

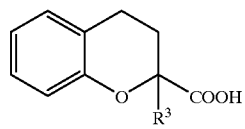

(II)

wherein R$^3$ is a hydrogen atom or an alkyl group, which method comprises reacting a dialkylphenol compound of the formula (III)

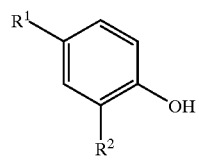

(III)

wherein R$^1$ and R$^2$ are each independently an alkyl group; a formaldehyde, and an alcohol in the presence of a secondary amine and an acid to give an alkoxymethylated phenol compound of the formula (IV)

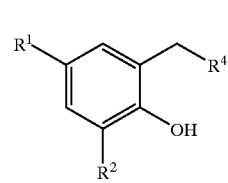

(IV)

wherein R$^1$ and R$^2$ are as defined above and R$^4$ is an alkoxyl group; reacting the obtained alkoxymethylated phenol compound with an ester of the formula (V)

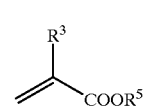

(V)

wherein R$^3$ is as defined above and R$^5$ is an alkyl group or an aralkyl group, having a carbon-carbon double bond, at a temperature of not less than 100° C. to give a dialkylchroman carboxylic acid ester of the formula (VI)

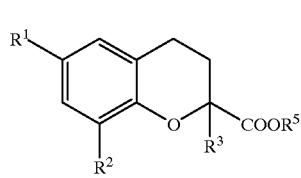

(VI)

wherein R$^1$, R$^2$, R$^3$ and R$^5$ are as defined above; hydrolyzing the obtained dialkylchroman carboxylic acid ester to give dialkylchroman-carboxylic acid of the formula (I)

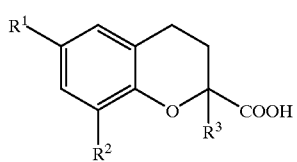

(I)

wherein R$^1$, R$^2$ and R$^3$ are as defined above; and reacting the obtained dialkylchroman-carboxylic acid with an aromatic hydrocarbon in the presence of a Lewis acid.

3. The method of claim 2, wherein the alkoxymethylated phenol compound of the formula (IV) and the ester of the formula (V), which has a carbon-carbon double bond, are reacted in the presence of an acid.

4. A dialkylchroman-carboxylic acid of the formula (I)

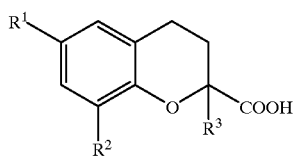

(I)

wherein R$^1$ and R$^2$ are each independently an alkyl group and R$^3$ is a hydrogen atom or an alkyl group.

5. The dialkylchroman-carboxylic acid of claim 4, wherein, in the formula (I), $R^1$ and $R^2$ are t-butyl group and $R^3$ is a hydrogen atom.

6. An alkoxymethylated phenol compound of the formula (IV)

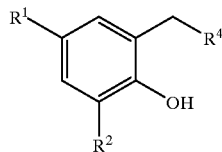

(IV)

wherein $R^1$ and $R^2$ are t-butyl group and $R^4$ is an alkoxyl group.

7. A method for producing a dialkylchroman-carboxylic acid of the formula (I)

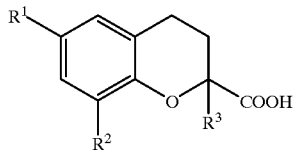

(I)

wherein $R^1$ and $R^2$ are each independently an alkyl group and $R^3$ is a hydrogen atom or an alkyl group, which method comprising reacting a dialkylphenol compound of the formula (III)

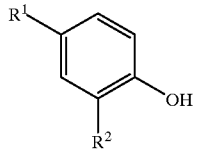

(III)

wherein $R^1$ and $R^2$ are as defined above, a formaldehyde and an alcohol in the presence of a secondary amine and an acid to give an alkoxymethylated phenol compound of the formula (IV)

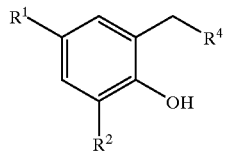

(IV)

wherein $R^1$ and $R^2$ are as defined above and $R^4$ is an alkoxyl group; reacting the obtained alkoxymethylated phenol compound with an ester of the formula (V)

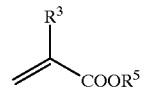

(V)

wherein $R^3$ is as defined above and $R^5$ is an alkyl group or an aralkyl group, having a carbon-carbon double bond, at a temperature of not less than 100° C. to give a dialkylchroman carboxylic acid ester of the formula (VI)

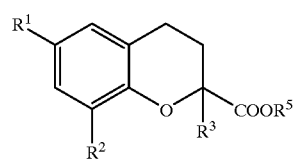

(VI)

wherein $R^1$, $R^2$, $R^3$ and $R^5$ are as defined above; and hydrolyzing the obtained dialkylchroman carboxylic acid ester.

8. The method of claim 1, wherein $R^1$, $R^2$ and $R^3$ are each independently a straight or branched chain alkyl group having one to eight carbon atoms.

9. The method of claim 1, wherein $R^1$ is a t-butyl group.

10. The method of claim 1, wherein $R^2$ is a t-butyl group.

11. The method of claim 1, wherein $R^3$ is a hydrogen atom.

12. The method of claim 2, wherein $R^1$, $R^2$ and $R^3$ are each independently a straight or branched chain alkyl group having one to eight carbon atoms.

13. The method of claim 2, wherein $R^4$ is an alkoxyl group having one to eight carbon atoms.

14. The method of claim 2, wherein $R^5$ is a straight or branched chain alkyl group having one to eight carbon atoms.

15. The method of claim 2, wherein $R^5$ is an aralkyl group having an aryl moiety with six to fourteen carbon atoms and having an alkyl moiety with one to six carbon atoms.

16. The dialkylchroman-carboxylic acid of claim 4, wherein $R^1$, $R^2$, and $R^3$ are each independently a straight or branched chain alkyl group having one to eight carbon atoms.

17. The alkoxymethylated phenol compound of claim 6, wherein $R^4$ is an alkoxyl group having one to eight carbon atoms.

18. The method of claim 7, wherein $R^1$, $R^2$, $R^3$, and $R^5$ are each independently a straight or branched chain alkyl group having one to eight carbon atoms.

19. The method of claim 7, wherein $R^4$ is an alkoxyl group having one to eight carbon atoms.

* * * * *